US010435349B2

(12) United States Patent
Chakraborty et al.

(10) Patent No.: US 10,435,349 B2
(45) Date of Patent: Oct. 8, 2019

(54) IRON-CATALYZED CROSS-COUPLING OF METHANOL WITH SECONDARY OR TERTIARY ALCOHOLS TO PRODUCE FORMATE ESTERS

(71) Applicant: Eastman Chemical Company, Kingsport, TN (US)

(72) Inventors: Sumit Chakraborty, Johnson City, TN (US); Steven J. Adams, Gray, TN (US); Robert Thomas Hembre, Johnson City, TN (US); Scott Donald Barnicki, Kingsport, TN (US); Michael Richard Laningham, Erwin, TN (US); Gerarld Wayne Ollis, Kingsport, TN (US); Randy Lynn Jennings, Gate City, VA (US)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 16/043,308

(22) Filed: Jul. 24, 2018

(65) Prior Publication Data

US 2019/0039992 A1 Feb. 7, 2019

Related U.S. Application Data

(60) Provisional application No. 62/540,317, filed on Aug. 2, 2017.

(51) Int. Cl.
| | |
|---|---|
| *C07C 69/013* | (2006.01) |
| *C07C 69/003* | (2006.01) |
| *C07C 67/00* | (2006.01) |
| *C07F 17/00* | (2006.01) |
| *C07F 15/00* | (2006.01) |
| *B01J 31/24* | (2006.01) |
| *C07F 15/02* | (2006.01) |
| *B01J 31/18* | (2006.01) |
| *B01J 31/20* | (2006.01) |

(52) U.S. Cl.
CPC .......... *C07C 69/013* (2013.01); *B01J 31/189* (2013.01); *B01J 31/20* (2013.01); *B01J 31/24* (2013.01); *C07C 67/00* (2013.01); *C07C 69/003* (2013.01); *C07F 15/0046* (2013.01); *C07F 15/025* (2013.01); *C07F 17/00* (2013.01); *B01J 2231/49* (2013.01); *B01J 2231/641* (2013.01); *B01J 2231/763* (2013.01); *B01J 2531/0244* (2013.01); *B01J 2531/842* (2013.01); *C01B 2203/0277* (2013.01); *C01B 2203/04* (2013.01); *C01B 2203/048* (2013.01)

(58) Field of Classification Search
CPC ........ C07C 69/013; C07C 67/00; B01J 31/24; B01J 2531/0244; C07F 15/025
See application file for complete search history.

(56) References Cited

U.S. PATENT DOCUMENTS

| | | |
|---|---|---|
| 1,400,195 A | 12/1921 | Willkie |
| 1,857,921 A | 5/1932 | Lazier |
| 1,999,403 A | 4/1935 | Dreyfus |
| 2,060,880 A | 11/1936 | Lazier |
| 2,152,182 A | 3/1939 | Ellis et al. |
| 2,305,104 A | 12/1942 | Pardee, Jr. |
| 2,504,497 A | 4/1950 | Charles et al. |
| 2,607,805 A | 8/1952 | Gresham |
| 3,911,003 A | 10/1975 | Suzuki |
| 4,052,424 A | 10/1977 | Vanderspurt |
| 4,076,594 A | 2/1978 | Buelow et al. |
| 4,112,245 A | 9/1978 | Zehner et al. |
| 4,149,009 A | 4/1979 | Yoneoka et al. |
| 4,214,106 A | 7/1980 | Freudenberger et al. |
| 4,216,339 A | 8/1980 | Couteau et al. |
| 4,217,460 A | 8/1980 | Hohenschutz et al. |
| 4,218,568 A | 8/1980 | Hohenschutz et al. |
| 4,232,171 A | 11/1980 | Yoneoka et al. |
| 4,319,037 A | 3/1982 | Yoneoka |
| 4,326,073 A | 4/1982 | Wolf et al. |
| 4,366,333 A | 12/1982 | Wilkes |
| 4,436,835 A | 3/1984 | Horie et al. |
| 4,440,873 A | 4/1984 | Miyazaki et al. |
| 4,453,026 A | 6/1984 | Tahara et al. |
| 4,480,122 A | 10/1984 | Horlenko et al. |
| 4,511,744 A | 4/1985 | Miyazaki et al. |

(Continued)

FOREIGN PATENT DOCUMENTS

| | | |
|---|---|---|
| CA | 1 238 919 A | 7/1988 |
| EP | 2 599 544 A1 | 6/2013 |

(Continued)

OTHER PUBLICATIONS

Bielinski et al, ACS Catalysis, Base-Free Methanol Dehydrogenation Using a Pincer-Supported Iron Compound and Lewis Acid Co-catalyst, 2015, 5, pp. 2404-2415 (Year: 2015).*
Chakraborty et al, ACS Catalysis, Well-Defined Iron Catalysts for the Acceptorless Reversible Dehydrogenation-Hydrogenation of Alcohols and Ketones, 2014, 4, pp. 3994-4003. (Year: 2014).*
Norskov et al, Nature Chemistry, Towards the Computational Design of Solid Catalysts, 2009, 1, pp. 37-46. (Year: 2009).*
Notice of Allowance dated Mar. 7, 2019 received in U.S. Appl. No. 16/043,317.
Notice of Allowance dated Mar. 7, 2019 received in U.S. Appl. No. 16/043,320.

(Continued)

*Primary Examiner* — Paul A Zucker
(74) *Attorney, Agent, or Firm* — Matthew W. Smith

(57) ABSTRACT

A process for preparing a variety of secondary and tertiary alkyl formate esters via the coupling of methanol and secondary (or tertiary) alcohols. Iron-based catalysts, supported by pincer ligands, are employed to produce these formate esters in high yields and unprecedentedly high selectivities (>99%). Remarkably, the coupling strategy is also applicable to bulkier tertiary alcohols, which afford corresponding tertiary formate esters in moderately high yields and high selectivities.

12 Claims, No Drawings

(56) References Cited

U.S. PATENT DOCUMENTS

| | | | |
|---|---|---|---|
| 4,601,909 A | 7/1986 | Nagoshi | |
| 4,677,234 A | 6/1987 | Bartley | |
| 4,792,620 A * | 12/1988 | Paulik | B01J 31/0231 |
| | | | 560/232 |
| 5,144,062 A | 9/1992 | Chen et al. | |
| 5,194,675 A | 3/1993 | Joerg et al. | |
| 5,206,433 A | 4/1993 | Hohenschutz et al. | |
| 6,376,723 B2 | 4/2002 | Drent et al. | |
| 6,455,742 B1 | 9/2002 | Cortright et al. | |
| 6,841,085 B2 | 1/2005 | Werpy et al. | |
| 6,956,134 B2 | 10/2005 | Liu et al. | |
| 7,615,671 B2 | 11/2009 | Puckette et al. | |
| 8,455,677 B2 | 6/2013 | Nakamura et al. | |
| 8,969,632 B2 | 3/2015 | Norman et al. | |
| 9,040,748 B2 | 5/2015 | Janka et al. | |
| 9,493,395 B2 | 11/2016 | Janka et al. | |
| 2015/0151289 A1 | 6/2015 | Mikhailine et al. | |
| 2015/0274621 A1 | 10/2015 | Fairweather et al. | |
| 2016/0318956 A1 | 11/2016 | Quintaine et al. | |
| 2016/0326202 A1 | 11/2016 | Morris et al. | |

FOREIGN PATENT DOCUMENTS

| | | |
|---|---|---|
| GB | 2 116 552 A | 9/1983 |
| WO | WO 82/03854 A1 | 11/1982 |
| WO | WO 2006/106483 A1 | 10/2006 |
| WO | WO 2006/106484 A1 | 10/2006 |
| WO | WO 2013/079659 A1 | 6/2013 |
| WO | WO 2015/091158 A1 | 6/2015 |
| WO | WO 2017/194663 A1 | 11/2017 |

OTHER PUBLICATIONS

Co-pending U.S. Appl. No. 16/043,303, filed Jul. 24, 2018; Chakraborty et al.

Co-pending U.S. Appl. No. 16/043,312, filed Jul. 24, 2018; Chakraborty et al.

Co-pending U.S. Appl. No. 16/043,317, filed Jul. 24, 2018; Chakraborty et al.

Notice of Allowance dated Nov. 15, 2018 received in U.S. Appl. No. 16/043,317.

Co-pending U.S. Appl. No. 16/043,320, filed Jul. 24, 2018; Chakraborty et al.

Notice of Allowance dated Nov. 2, 2018 received in U.S. Appl. No. 16/043,320.

Notice of Allowance dated Nov. 15, 2018 received in U.S. Appl. No. 16/043,320.

Co-pending U.S. Appl. No. 16/043,324, filed Jul. 24, 2018; Barnicki et al.

Co-pending U.S. Appl. No. 16/043,329, filed Jul. 24, 2018; Barnicki et al.

Wittstock et al.; "Nanoporous Gold Catalysts for Selective Gas-Phase Oxidative Coupling of Methanol at Low Temperature;" Science; 2010; vol. 327; pp. 319-323.

Wang et al.; "Graphene-supported Au—Pd bimetallic nanoparticles with excellent catalytic performance in selective oxidation of methanol to methyl formate;" Chem. Commun., 2013, 49, pp. 8250-8252.

Liu et al.; "Methanol Selective Oxidation to Methyl Formate over $ReO_x/CeO_2$ Catalysts;" Catal. Lett.; 2008; 120; pp. 274-280.

Huang et al.; "Effect of treatment temperature on structures and properties of zirconia-supported ruthenium oxide catalysts for selective oxidation of methanol to methyl formate;" Catalysis Today; 2012; 183; pp. 58-64.

Kaichev et al.; "Selective oxidation of methanol to form dimethoxymethane and methyl formate over a monolayer $V_2O_5/TiO_2$ catalyst;" Journal of Catalysis; 2014; 311; pp. 59-70.

Itagaki et al.; "Transition Metal Homogeneous Catalysis for Liquid-Phase Dehydrogenation of Methanol;" Journal of Molecular Catalysis; 1987; 41; pp. 209-220.

Smith et al.; "The Ruthenium-Catalysed Conversion of Methanol into Methyl Formate;" Journal of Organometallic Chemistry; 1985; 291; pp. C13-C14.

Yang et al.; "Mechanistic study on dehydrogenation of methanol with $[RuCl_2(PR_3)_3]$-type catalyst in homogeneous solutions;" Journal of Molecular Catalysis A: Chemical; 1996; 108; pp. 87-93.

Yamakawa et al.; "Catalytic Reaction of Methanol with a Series of Ruthenium (II) Complexes and the Mechanism of the Formation of Acetic Acid from Methanol Alone;" J. Chem. Soc. Dalton Trans.; 1994; pp. 2265-2269.

Shinoda et al.; "One-step Formation of Methyl Acetate with Methanol used as the Sole Source and Catalysis by Ru"-Sn" Cluster Complexes;" J. Chem. Soc., Chem. Commun.; 1990; pp. 1511-1512.

Kuriyama et al.; "Catalytic Hydrogenation of Esters. Development of an Efficient Catalyst and Processes for Synthesising (R)-1,2-Propanediol and 2-(I-Menthoxy)ethanol;" Org. ProcessRes. Dev.; 2012; 16; pp. 166-171.

Liu et al.; "Towards a Sustainable Synthesis of Formate Salts: Combined Catalytic Methanol Dehydrogenation and Bicarbonate Hydrogenation;" Angew. Chem. Int. Ed.; 2014; 53; pp. 7085-7088.

Alberico et al.; "Selective Hydrogen Production from Methanol with a Defined Iron Pincer Catalyst under Mild Conditions;" Angew. Chem. Int. Ed.; 2013; 52; pp. 14162-14166.

Werkmeister et al.; "Pincer-Type Complexes for Catalytic (De)Hydrogenation and Transfer (De)Hydrogenation Reactions: Recent Progress;" Chem. Eur. J.; 2015; 21; pp. 12226-12250.

Chakraborty et al.; "Nickel and Iron Pincer Complexes as Catalysts for the Reduction of Carbonyl Compounds;" Acc. Chem. Res.; 2015; 48; pp. 1995-2003.

Blum et al.; "Catalytically Reactive Ruthenium Intermediates in the Homogeneous Oxidation of Alcohols to Esters;" Israel Journal of Chemistry; vol. 24; 1984; pp. 144-148.

Blum et al.; "Structure of "$\eta^4$-$Ph_4C_4CO)(CO)_3Ru$—a Catalyst Precursor in H-Transfer and Dehydrogenation Reactions of Alcohols;" Inorganica Chimica Acta; 1985; 97; pp. L25-L26.

Warner et al.; "Shvo's Catalyst in Hydrogen Transfer Reactions;" Top Organomet Chem; 2011; 37; pp. 85-125.

Zhang et al.; "Facile Conversion of Alcohols into Esters and Dihydrogen Catalyzed by New Ruthenium Complexes;" J. Am. Chem. Soc.; 2005; 127; pp. 10840-10841.

Gunanathan et al.; "Direct Conversion of Alcohols to Acetals and H2 Catalyzed by an Acridine-Based Ruthenium Pincer Complex;" J. Am. Chem. Soc.; 2009; 131; pp. 3146-3147.

Zhang et al.; "Electron-Rich PNP- and PNN-Type Ruthenium(II) Hydrido Borohydride Pincer Complexes. Synthesis, Structure, and Catalytic Dehydrogenation of Alcohols and Hydrogenation of Esters;" Organometallics; 2011; 30; pp. 5716-5724.

Chakraborty et al.; "A Molecular Iron Catalyst for the Acceptorless Dehydrogenation and Hydrogenation of N-Heterocycles;" J. Am. Chem. Soc.; 2014; 136; pp. 8564-8567.

Chakraborty et al.; "Well-Defined Iron Catalysts for the Acceptorless Reversible Dehydrogenation-Hydrogenation of Alcohols and Ketones;" ACS Catal.; 2014; 4; pp. 3994-4003.

Chakraborty et al.; "Iron-Based Catalysts for the Hydrogenation of Esters to Alcohols;" J. Am. Chem. Soc.; 2014; 136; pp. 7869-7872.

Srimani et al.; "Ruthenium Pincer-Catalyzed Cross-Dehydrogenative Coupling of Primary Alcohols with Secondary Alcohols under Neutral Conditions;" Adv. Synth. Catal.; 2012; 354; pp. 2403-2406.

Hu et al.; "Rechargeable Hydrogen Storage System Based on the Dehydrogenative Coupling of Ethylenediamine with Ethanol;" Angew. Chem. Int. Ed.; 2016; 55; pp. 1061-1064.

Kim et al.; "Ruthenium-Catalyzed Urea Synthesis Using Methanol as the C1 Source;" Org. Lett.; 2016; 18; pp. 212-215.

Crabtree, Robert H.; "Resolving Heterogeneity Problems and Impurity Artifacts in Operationally Homogeneous Transition Metal Catalysts;" Chem. Rev.; 2012; 112; pp. 1536-1554.

Gnanadesikan et al.; "Direct Catalytic Asymmetric Aldol-Tishchenko Reaction;" J. Am. Chem. Soc.; 2004; 126; pp. 7782-7783.

Haslam, Edwin; "Tetrahedron Report No. 93—Recent Developments in Methods for the Esterification and Protection of the Carboxyl Group;" Tetrahedron; 1980; vol. 36; pp. 2409-2433.

Gregory et al.; "The Production of Ethyl Acetate From Ethylene and Acetic Acid Using Clay Catalysts;" Clay Minerals; 1983; 18; pp. 431-435.

(56) References Cited

OTHER PUBLICATIONS

Goldemberg, José; "Ethanol for a Sustainable Energy Future;" Science; 2007; vol. 315; pp. 808-810.

Wang et al.; "Direct transformation of ethanol to ethyl acetate on Cu/ZrO2 catalyst;" Reac. Kinet. Mech. Cat.; 2010; 101; pp. 365-375.

Inui et al.; "Effective formation of ethyl acetate from ethanol over Cu—Zn—Zr—Al—O catalyst;" Journarl of Molecular Catalysis A: Chemical; 2004; 216; pp. 147-156.

Zonetti et al.; "Chemicals from ethanol—the dehydrogenative route of the ethyl acetate one-pot synthesis;" Journal of Molecular Catalysis A: Chemical; 2011; 334; pp. 29-34.

Medeiros et al.; "The role of water in ethanol oxidation over SnO2-supported molybdenum oxides;" Catalysis Letters; 69; 2000; pp. 79-82.

Gunanathan et al.; "Applications of Acceptorless Dehydrogenation and Related Transformations in Chemical Synthesis;" Science; 2013; vol. 341; pp. 249.

Bertoli et al.; "Osmium and Ruthenium Catalysts for Dehydrogenation of Alcohols;" Organometallics; 2011; 30; pp. 3479-3482.

Nielsen et al.; "Efficient Hydrogen Production from Alcohols under Mild Reaction Conditions;" Angew. Chem. Int. Ed.; 2011; 50; pp. 9593-9597.

Morton et al.; "Molecular Hydrogen Complexes in Catalysis: Highly Efficient Hydrogen Production from Alcoholic Substrates catalyzed by Ruthenium Complexes;" J. Chem. Soc., Chem. Commun.; 1988; pp. 1154-1156.

Nielsen et al.; "Towards a Green Process for Bulk-Scale Synthesis of Ethyl Acetate: Efficient Acceptorless Dehydrogenation of Ethanol;" Angew. Chem. Int. Ed.; 2012; 51; pp. 5711-5713.

Carlini et al.; "Selective synthesis of isobutanol by means of the Guerbet reaction Part 2. Reaction of methanol/ethanol and methanol/ethanol/n-propanol mixtures over copper based/MeONa catalytic systems;" Journal of Molecular Catalysis A: Chemical; 200; 2003; pp. 137-146.

Furukawa et al.; "High Polymerization of Acetaldehyde by Alumina—A New Method of Preparation of Polyether;" Journal of Polymer Science; vol. XXXVI; Issue No. 130; 1959; pp. 546.

Degering et al.; "Polymerization of Acetaldehyde and Crotonaldehyde Catalyzed by Aliphatic Tertiary Amines;" Journal of Polymer Science; vol. VII; No. 6; pp. 653-656.

Teunissen et al.; "Ruthenium catalyzed hydrogenation of dimethyl oxalate to ethylene glycol;" Chem. Commun.; 1997; pp. 667-668.

Zhang et al.; "Efficient Homogeneous Catalytic Hydrogenation of Esters to Alcohols;" Angew. Chem. Int. Ed.; 2006; 45; pp. 1113-1115.

Saudan et al.; "Dihydrogen Reduction of Carboxylic Esters to Alcohols under the Catalysis of Homogeneous Ruthenium Complexes: High Efficiency and Unprecedented Chemoselectivity;" Angew. Chem. Int. Ed.; 2007; 46; pp. 7473-7476.

Dub et al.; "Catalytic Reductive Transformations of Carboxylic and Carbonic Acid Derivatives Using Molecular Hydrogen;" ACS Catal.; 2012; 2; pp. 1718-1741.

Clarke, Matthew L.; "Recent developments in the homogeneous hydrogenation of carboxylic acid esters;" Catal. Sci. Technol.; 2012; 2; pp. 2418-2423.

Chakraborty et al.; "First-row transition metal catalyzed reduction of carbonyl functionalities: a mechanistic perspective;" Dalton Trans.; 2010; 39; pp. 7427-7436.

Zell et al.; "Unprecedented Iron-Catalyzed Ester Hydrogenation. Mild, Selective, and Efficient Hydrogenation of Trifluoroacetic Esters to Alcohols Catalyzed by an Iron Pincer Complex;" Angew. Chem. Int. Ed.; 2014; 53; pp. 4685-4689.

Werkmeister et al.; "Hydrogenation of Esters to Alcohols with a Well-Defined Iron Complex;" Angew. Chem. Int. Ed.; 2014; 53; pp. 8722-8726.

Wang et al.; "The Golden Age of Transfer Hydrogenation;" Chem. Rev.; 2015; 115; pp. 6621-6686.

Lee et al.; "Transfer Hydrogenation of Ketones, Nitriles, and Esters Catalyzed by a Half-Sandwich Complex of Ruthenium;" ChemCatChem; 2015; 7; pp. 107-113.

Dubey et al.; "Catalytic Ester Metathesis Reaction and Its Application to Transfer Hydrogenation of Esters;" ACS Catal.; 2016/ 6; pp. 3998-4002.

Dusselier et al.; "Lactic acid as a platform chemical in the biobased economy: the role of chemocatalysis;" Energy Environ. Sci.; 2013; 6; pp. 1415-1442.

Carnahan et al.; "Ruthenium-catalyzed Hydrogenation of Acids to Alcohols;" Journal of the American Chemical Society; 1955; vol. 77; Issue 14; pp. 3766-3768.

Matteoli et al.; "Structure and catalytic activity of phosphine-substituted ruthenium carbonyl carboxylates;" Journal of Organometallic Chemistry; 498; 1995; pp. 177-186.

http://www.ube-ind.co.jp/ube/en/news/2015/20160316_01.html Ube Industries Licenses DMC Technology and Agrees to Establish Joint Venture for High-Purity DMC.

Vom Stein et al.; "Highly Versatile Catalytic Hydrogenation of Carboxylic and Carbonic Acid Derivatives using a Ru-Triphos Complex: Molecular Control over Selectivity and Substrate Scope;" J. Am. Chem. Soc.; 2014; 136; pp. 13217-13225.

Shuklov et al.; "Propane-1,2-diols from Dilactides, Oligolactides, or Poly-L-Lactic Acid (PLLA): From Plastic Waste to Chiral Bulk Chemicals;" Chem. Eur. J.; 2014; 20; pp. 957-960.

Spasyuk et al.; "Acceptorless Dehydrogenative Coupling of Ethanol and Hydrogenation of Esters and Imines;" Organometallics; 2012; 31; pp. 5239-5242.

Fan et al.; "Efficient Hydrogenation of Ethyl Lactate to 1,2-Propanediol over Ru-B/TiO$_2$ in Aqueous Solution;" Chemistry Letters; vol. 37, No. 8; 2008; pp. 852-853.

Zhang et al.; "Aqueous-phase hydrogenation of lactic acid to propylene glycol;" Applied Catalysis A: General; 2001; 219; pp. 89-98.

Adkins et al.; "The Hydrogenation of Esters to Alcohols at 25-150°;" Journal of the American Chemical Society; 1948; vol. 70; Issue 9; pp. 3121-3125.

Broadbent et al.; "Rhenium and Its Compounds as Hydrogenation Catalysts. III. Rhenium Heptoxide;" Journal of Organic Chemistry; 1959; vol. 24; Issue 12; pp. 1847-1854.

Hietala et al.; "Formic Acid"; Ullmann's Encyclopedia of Industrial Chemistry; vol. 16; 2012; Wiley-VCH Verlag GmbH & Co. KGaA, Weinheim; pp. 13-33.

Di Girolamo et al.; "Acidic and basic ion exchange resins for industrial applications;" Journal of Molecular Catalysis A: Chemical; 2001; 177; pp. 33-40.

Nørskov et al.; "Towards the computational design of solid catalysts;" Nature Chemistry; vol. 1; Apr. 2009; pp. 37-46.

Bielinski et al.; "Base-Free Methanol Dehydrogenation Using a Pincer-Supported Iron Compound and Lewis Acid Co-catalyst;" ACS Catal.; 2015; 5; pp. 2404-2415.

Fairweather et al.; "Homogeneous Hydrogenation of Fatty Acid Methyl Esters and Natural Oils under Neat Conditions;" Organometallics; 2015; 34; pp. 335-339.

Qu et al.; "Computational Mechanistic Study of Fe-Catalyzed Hydrogenation of Esters to Alcohols: Improving Catalysis by Accelerating Precatalyst Activation with a Lewis Base;" ACS Catal.; 2014; 4; pp. 4377-4388.

Notification of Transmittal of the International Search Report and the Written Opinion of the International Searching Authority dated Oct. 19, 2018 for International Application No. PCT/US2018/044482.

Notification of Transmittal of the International Search Report and the Written Opinion of the International Searching Authority dated Oct. 19, 2018 for International Application No. PCT/US2018/044485.

Monnereau et al.; "Efficient Synthesis of Differentiated syn-1,2-Diol Derivatives by Asymmetric Transfer Hydrogenation-Dynamic Kinetic Resolution of α-Alkoxy-Substituted β-Ketoesters;" Chemistry—A European Journal; 2015; 21; pp. 11799-11806.

Kim et al.; "Transfer Hydrogenation of Organic Formates and Cyclic Carbonates: An Alternative Route to Methanol from Carbon Dioxide;" ACS Catal.; 2014; 4; pp. 3630-3636.

(56) References Cited

OTHER PUBLICATIONS

Patil et al.; "Immobilized Iron Metal-Containing Ionic Liquid-Catalyzed Chemoselective Transfer Hydrogenation of Nitroarenes into Anilines;" ACS Sustainable Chem. Eng.; 2016; 4; pp. 429-436.

Notification of Transmittal of the International Search Report and the Written Opinion of the International Searching Authority dated Oct. 19, 2018 for International Application No. PCT/US2018/044476.

Notification of Transmittal of the International Search Report and the Written Opinion of the International Searching Authority dated Oct. 26, 2018 for International Application No. PCT/US2018/044518.

Pandey et al.; "Acceptorless Alcohol Dehydrogenation: A Mechanistic Perspective;" Proc. Natl. Acad. Sci., India, Sect. A Phys. Sci.; 2016; vol. 86; Issue 4; pp. 561-579.

Notification of Transmittal of the International Search Report and the Written Opinion of the International Searching Authority dated Oct. 26, 2018 for International Application No. PCT/US2018/044512.

Iranpoor et al.; "Silphos [$PCl_{3-n}(SiO_2)_n$]: a heterogeneous phosphine reagent for formylation and acetylation of alcohols and amines with ethyl formate and acetate;" Tetrahedron Letters; 46; 2005; pp. 7963-7966.

Lane et al.; "Iron-Catalyzed Amide Formation from the Dehydrogenative Coupling of Alcohols and Secondary Amines;" Organometallics; 2017; 36; pp. 2020-2025.

Notification of Transmittal of the International Search Report and the Written Opinion of the International Searching Authority dated Oct. 26, 2018 for International Application No. PCT/US2018/044506.

Notification of Transmittal of the International Search Report and the Written Opinion of the International Searching Authority dated Nov. 6, 2018 for International Application No. PCT/US2018/044521.

Office Action dated Apr. 5, 2019 received in U.S. Appl. No. 16/043,329.

Chintan et al.; "Separation of azeotropic mixture of formic acid-water by using Li—Br as a salt by extractive distillation;" IJARIIE-ISSN (O)-2395-4396; vol. 2; Issue 3; 2016; pp. 607-612.

\* cited by examiner

IRON-CATALYZED CROSS-COUPLING OF METHANOL WITH SECONDARY OR TERTIARY ALCOHOLS TO PRODUCE FORMATE ESTERS

CROSS REFERENCE TO RELATED APPLICATION

This application claims the benefit of Provisional Application 62/540,317 filed on Aug. 2, 2017 under 35 U.S.C. § 119(e)(1), the entire content of which is incorporated herein by reference.

FIELD OF THE INVENTION

This invention generally belongs to the field of organic chemistry. It particularly relates to a process for preparing secondary and tertiary alkyl formate esters.

BACKGROUND OF THE INVENTION

Formic acid is typically produced commercially by a two-step process. Methanol is first carbonylated to yield methyl formate. Then, the methyl formate is hydrolyzed to generate formic acid and methanol. Although the carbonylation of methanol is a straightforward process, the hydrolysis of methyl formate to form formic acid has a very poor equilibrium constant ($K_{eq} \approx 0.2$ at 25° C.). As a result, the maximum yield of formic acid from this process is very low.

A possible solution to this problem would be to use other alkyl formate species that have better hydrolysis equilibria. While direct carbonylation of secondary and tertiary alcohols is a viable route to produce these other formate species, the carbonylation reactions, especially ones involving tertiary alcohols, are generally low-yielding and often require higher temperatures and much higher carbon monoxide pressures.

Accordingly, there is a need for more efficient and greener processes for synthesizing secondary and tertiary formate esters from methanol, particularly without using the toxic CO gas.

The present invention addresses this need as well as others, which will become apparent from the following description and the appended claims.

SUMMARY OF THE INVENTION

The invention is as set forth in the appended claims.

Briefly, the invention provides a process for preparing a formate ester of the formula (X):

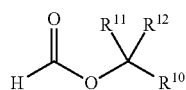

wherein $R^{10}$, $R^{11}$, and $R^{12}$ are each independently hydrogen or an alkyl group having 1 to 6 carbon atoms, provided that no more than one of $R^{10}$, $R^{11}$, and $R^{12}$ is hydrogen;

$R^{11}$ and $R^{12}$ may be connected to form a cycloaliphatic group having 4 to 8 carbon atoms; and $R^{10}$, $R^{11}$, and $R^{12}$ may be connected to form a bicycloaliphatic group having 5 to 14 carbon atoms.

The process comprises contacting anhydrous methanol with an alcohol of the formula (XI):

in the presence of a catalyst of the formula (I):

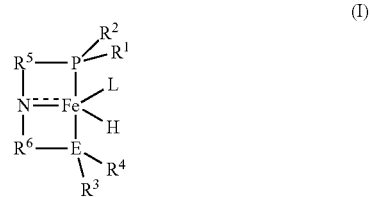

in a reactor at conditions effective to form the formate ester of the formula (X).

The contacting step is conducted in the presence of a hydrogen acceptor, or with the simultaneous removal of hydrogen from the reactor, or both.

R1 and R2 in the formula (I) are each independently an alkyl, aryl, alkoxy, aryloxy, dialkylamido, diarylamido, or alkylarylamido group having 1 to 12 carbon atoms;

R3 and R4 in the formula (I) are each independently an alkyl or aryl group having 1 to 12 carbon atoms, if E is nitrogen.

R3 and R4 in the formula (I) are each independently an alkyl, aryl, alkoxy, aryloxy, dialkylamido, diarylamido, or alkylarylamido group having 1 to 12 carbon atoms, if E is phosphorus.

R1, R2, and P may be connected to form a 5 or 6-membered heterocyclic ring.

R3, R4, and E may be connected to form a 5 or 6-membered heterocyclic ring.

R5 and R6 in the formula (I) are each independently a C1-C6 alkylene or arylene group.

E in the formula (I) is phosphorus or nitrogen.

L in the formula (I) is a neutral ligand.

$R^{10}$, $R^{11}$, and $R^{12}$ in the formula (XI) are as defined in the formula (X).

DETAILED DESCRIPTION OF THE INVENTION

It has been surprisingly discovered that formate ester derivatives can be directly produced, in high yields, by performing a dehydrogenative coupling (DHC or dehydrocoupling) reaction of methanol with a secondary or tertiary alcohol in the presence of a homogeneous iron catalyst containing a tridentate pincer ligand. This reaction does not require the use of toxic, pressurized CO gas and has the added value of co-producing dihydrogen as the main by-product.

Thus, in one aspect, the present invention provides a process for preparing a formate ester of the formula (X):

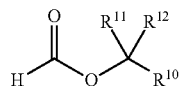
(X)

wherein $R^{10}$, $R^{11}$, and $R^{12}$ are each independently hydrogen or an alkyl group having 1 to 6 carbon atoms, provided that no more than one of $R^{10}$, $R^{11}$, and $R^{12}$ are hydrogen;

$R^{10}$, $R^{11}$, and $R^{12}$ may be independently substituted with an alcohol or formate group;

$R^{11}$ and $R^{12}$ may be connected to form a cycloaliphatic group having 4 to 8 carbon atoms; and $R^{10}$, $R^{11}$, and $R^{12}$ may be connected to form a bicycloaliphatic group having 5 to 14 carbon atoms.

Examples of compounds having the formula (X) include isopropyl formate; 2-butyl formate; tert-butyl formate; cyclohexyl formate; 1-methyl-cyclohexyl formate; 1-propoxy-2-propanyl formate; 1-ethoxy-2-propanyl formate; 1-methoxy-2-propanyl formate; 1,4-diformyloxy-bicyclo[2.2.2]octane; 1,3-diformyloxy-tricyclo[3.3.1.1]decane (1,3-diformyloxyadamantane); 1,4-diformyloxy dimethylcyclohexane; and 1,2-diformyloxycyclohexane.

The process comprises the step of contacting anhydrous methanol with an alcohol of the formula (XI):

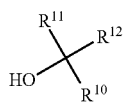
(XI)

in the presence of a catalyst of the formula (I):

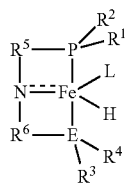
(I)

in a reactor at conditions effective to form the formate ester of the formula (X).

The contacting step is conducted in the presence of a hydrogen acceptor, or with the simultaneous removal of hydrogen from the reactor, or both. In one embodiment, the contacting step/DHC reaction is conducted in the presence of a hydrogen acceptor. In another embodiment, the contacting step/DHC reaction is conducted in the absence of a hydrogen acceptor, but with the simultaneous removal of hydrogen from the reactor. In yet another embodiment, the contacting step/DHC reaction is conducted with the simultaneous removal of hydrogen from the reactor.

As used herein, the term "hydrogen acceptor" refers to any substance that can become reduced by accepting one or more hydrogen atoms under DHC reaction conditions. Examples of hydrogen acceptors useful in the invention include acetone, methyl methacrylate, isophorone, cyclohexene, styrene, 2-ethylhex-2-enal, and combinations thereof.

If used, the hydrogen acceptor may be added at a methanol-to-acceptor molar ratio of 1:1 to 1:10, or 1:1 to 1:5.

R10, R11, and R12 in the formula (XI) are as defined in the formula (X).

The formula (XI) represents secondary and tertiary alcohols. Examples of such alcohols include isopropanol, 2-butanol, tert-butanol, cyclohexanol, 1-methyl-cyclohexanol, propylene glycol propyl ether, 1-propoxy-2-propanol, 1-ethoxy-2-propanol, and 1-formyloxy-2-propanol. Such alcohols also include diols, such as bicyclo[2.2.2]octane-1,4-diol; tricyclo[3.3.1.1]decane-1,3-diol (adamantane-1,3-diol); 1,4-dimethylcyclohexane-1,4-diol; and 1,2-cyclohexanediol.

R1 and R2 in the formula (I) are each independently an alkyl, aryl, alkoxy, aryloxy, dialkylamido, diarylamido, or alkylarylamido group having 1 to 12 carbon atoms.

R3 and R4 in the formula (I) are each independently an alkyl or aryl group having 1 to 12 carbon atoms, if E is nitrogen.

R3 and R4 in the formula (I) are each independently an alkyl, aryl, alkoxy, aryloxy, dialkylamido, diarylamido, or alkylarylamido group having 1 to 12 carbon atoms, if E is phosphorus.

R5 and R6 in the formula (I) are each independently a C1-C6 alkylene or arylene group.

E in the formula (I) is phosphorus or nitrogen.

L in the formula (I) is a neutral ligand.

$R^1$, $R^2$, and P in the formula (I) may be connected to form a 5 or 6-membered heterocyclic ring.

R3, R4, and E in the formula (I) may be connected to form a 5 or 6-membered heterocyclic ring.

One or more of R1, R2, R3, and R4 may be substituted with one or more groups selected from ethers, esters, and amides. The substituents on R1, R2, R3, and R4, if any, may be the same or different.

Examples of ether groups include methoxy, ethoxy, isopropoxy, and the like.

Examples of ester groups include formate, acetate, propionate, and the like.

Examples of amide groups include dimethylamido, diethylamido, diisopropylamido, and the like.

As used herein, the term "alkyl" refers to straight, branched, or cyclic alkyl groups. Examples of such groups include methyl, ethyl, n-propyl, isopropyl, n-butyl, sec-butyl, isobutyl, tert-butyl, n-pentyl, tert-pentyl, neopentyl, isopentyl, sec-pentyl, 3-pentyl, cyclopentyl, n-hexyl, isohexyl, cyclohexyl, and the like.

The term "aryl" refers to phenyl or naphthyl.

The term "alkylene" refers to a divalent alkyl group.

The term "arylene" refers to a divalent aryl group.

The term "alkoxy" refers to an —OR group, such as —OCH3, —OEt, —OiPr, —OBu, —OiBu, and the like.

The term "aryloxy" refers to an —OAr group, such as —OPh, —O(substituted Ph), -Onaphthyl, and the like.

The term "dialkylamido" refers to an —NR'R" group, such as dimethylamido, diethylamido, diisopropylamido, and the like.

The term "diarylamido" refers to an —NAr'Ar" group, such as diphenylamido.

The term "alkylarylamido" refers to an —NRAr group, such as methylphenylamido.

The term "neutral ligand" refers to a ligand with a neutral charge. Examples of neutral ligands include carbon monoxide, an ether compound, an ester compound, a phosphine compound, an amine compound, an amide compound, a nitrile compound, and an N-containing heterocyclic compound. Examples of neutral phosphine ligands include trimethylphosphine, tricyclohexylphosphine, triphenylphosphine, and the like. Examples of neutral amine ligands include trialkylamines, alkylarylamines, and dialkylarylamines, such as trimethylamine and N,N-dimethylanaline. Examples of neutral nitrile ligands include acetonitrile. Examples of neutral N-containing heterocyclic ligands include pyridine and 1,3-dialkyl- or diaryl-imidazole carbenes.

In one embodiment, R1, R2, R3, and R4 are all isopropyl. In another embodiment, R1, R2, R3, and R4 are all phenyl.

In one embodiment, R5 and R6 are both —(CH2CH2)-.

In one embodiment, E is phosphorus.

In various embodiments, the catalyst of the formula (I) has the formula (1C):

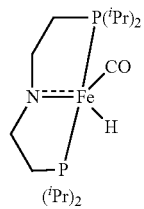

(1C)

where $^{i}$Pr represents an isopropyl group.

Anhydrous methanol is commercially available in various grades, such as >99 wt % of methanol, 99-100 wt % of methanol, 99.7 wt % of methanol, 99.8 wt % of methanol, and 100 wt % of methanol. Any of these grades may be used in the DHC reaction.

Preferably, the reaction mixture contains less than 1 wt %, less than 0.5 wt %, less than 0.4 wt %, less than 0.3 wt %, less than 0.2 wt %, less than 0.1 wt %, less than 0.05 wt %, less than 0.01 wt %, less than 0.005 wt %, or less than 0.001 wt % of water, based on the total weight of the reaction mixture. In one embodiment, the DHC reaction is carried out in the absence of water.

The catalyst of the formula (I) may be prepared in multiple ways. For example, the catalyst may be formed in situ by introducing a pre-catalyst of the formulas (IIa) or (IIb):

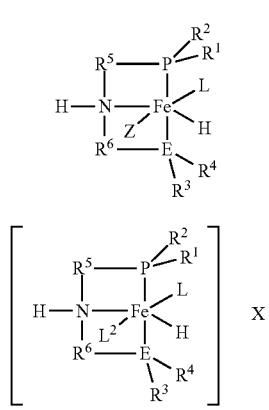

(IIa)

(IIb)

into the reactor and exposing the pre-catalyst to heat, an acid, a base, or combinations thereof to form the catalyst of the formula (I).

R1, R2, R3, R4, R5, R6, E, and L in the formulas (IIa) or (IIb) are as defined in formula (I).

Z in the formula (IIa) is R7 or X.

R7 is hydrogen or an alkyl or aryl group.

X is [BH4]- or a halide.

L2 in the formula (IIb) is a neutral ligand.

The alkyl or aryl group represented by R7 may contain from 1 to 12 carbon atoms.

The halides represented by X include chloride, bromide, and iodide. In one embodiment, X is chloride or bromide.

Examples of the neutral ligand L2 include an ether compound, an ester compound, an amide compound, a nitrile compound, and an N-containing heterocyclic compound.

In one embodiment, when X is a halide, the pre-catalyst is exposed to a base and optionally to heat to generate the catalyst.

In another embodiment, when X is [BH4]-, the pre-catalyst is exposed to heat, but optionally in the absence of a base, to generate the catalyst.

As used herein, the expression "in the absence of" means the component referred to is not added from an external source or, if added, is not added in an amount that affects the DHC reaction to an appreciable extent, for example, an amount that can change the yield of the formate ester by more than 10%, by more than 5%, by more than 1%, by more than 0.5%, or by more than 0.1%.

In various embodiments, the pre-catalyst of the formula (IIa) has the formula (1B):

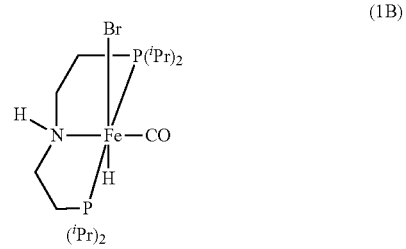

(1B)

where $^{i}$Pr represents an isopropyl group.

In various embodiments, the pre-catalyst of the formula (IIb) has the formula (1A):

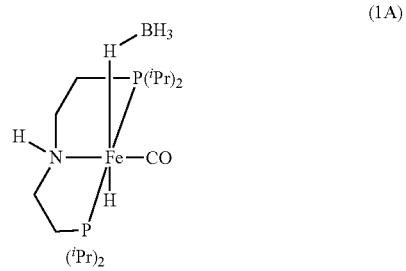

(1A)

where $^{i}$Pr represents an isopropyl group.

Alternatively, the catalyst of the formula (I) may be formed in situ by the steps of:

(a) introducing (i) an iron salt or an iron complex comprising the neutral ligand (L), (ii) a ligand of the formula (III):

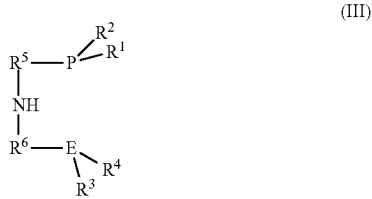

and (iii) optionally the neutral ligand (L) into the reactor to form a pre-catalyst mixture; and (b) optionally exposing the pre-catalyst mixture to heat, an acid, a base, or combinations thereof to form the catalyst of the formula (I).

R1, R2, R3, R4, R5, R6, and E in the formula (III) are as defined in formula (I).

Examples of iron salts suitable for making the catalyst of the formula (I) include [Fe(H2O)6](BF4)2, Fe(CO)5, FeCl2, FeBr2, FeI2, [Fe3(CO)12], Fe(NO3)2, FeSO4, and the like.

Iron complexes comprising the neutral ligand (L) may be made by methods known in the art and/or are commercially available.

Ligands of the formula (III) may be made by methods known in the art and/or are commercially available.

The heat employed for generating the catalyst is not particularly limiting. It may be the same as the heat used for the DHC reaction. For example, the pre-catalyst or pre-catalyst mixture may be exposed to elevated temperatures, such as from 40 to 200° C., 40 to 160° C., 40 to 150° C., 40 to 140° C., 40 to 130° C., 40 to 120° C., 40 to 100° C., 80 to 160° C., 80 to 150° C., 80 to 140° C., 80 to 130° C., 80 to 120° C., or 80 to 100° C., to form the catalyst.

The acid for forming the catalyst is not particularly limiting. Examples of suitable acids include formic acid, HBF$_4$, HPF$_6$, HOSO$_2$CF$_3$, and the like.

The base for forming the catalyst is not particularly limiting. Both inorganic as well as organic bases may be used. Examples of suitable inorganic bases include Na, K, NaH, NaOH, KOH, CsOH, LiHCO3, NaHCO3, KHCO3, CsHCO3, Li2CO3, Na2CO3, K2CO3, Cs2CO3, and the like. Suitable organic bases include metal alkoxides and nitrogen-containing compounds. Examples of suitable metal alkoxides include alkali-metal C1-C6 alkoxides, such as LiOEt, NaOEt, KOEt, and KOt-Bu. In one embodiment, the base is sodium methoxide (NaOMe). In another embodiment, the base is sodium ethoxide (NaOEt). Examples of nitrogen-containing bases include trialkylamines, such as triethylamine.

Typically, a 1:1 molar equivalent of base to catalyst precursor is used to generate the catalyst. More than a 1:1 molar equivalent ratio may be used, e.g., a 2:1 ratio of base to catalyst precursor. However, using a large excess amount of base should be avoided, as it may suppress the formation of the formate ester.

The conditions effective for forming the formate ester of the formula (X) include an elevated temperature. The temperature conducive for the DHC reaction may range, for example, from 40 to 200° C., 40 to 160° C., 40 to 150° C., 40 to 140° C., 40 to 130° C., 40 to 120° C., 40 to 100° C., 80 to 160° C., 80 to 150° C., 80 to 140° C., 80 to 130° C., 80 to 120° C., or 80 to 100° C.

The pressure at which the dehydrocoupling reaction may be carried out is not particularly limiting. For example, the pressure may range from atmospheric to 2 MPa. The reaction may be performed in an open reactor where the produced hydrogen is withdrawn as the reaction proceeds. Alternatively, the reaction may be performed in a sealed reactor, but in the presence of a hydrogen acceptor.

Preferably, the contacting step/dehydrocoupling reaction is carried out in the absence of a base. Basic conditions during the reaction may tend to suppress the formation of the formate ester.

The dehydrocoupling reaction may be conducted in the presence or absence of a solvent. In one embodiment, the contacting step/DHC reaction is conducted in the presence of a solvent. In another embodiment, the contacting step/DHC reaction is conducted in the absence of a solvent.

If desired, the DHC reaction may be performed in common non-polar solvents, such as aliphatic or aromatic hydrocarbons, or in slightly polar, aprotic solvents, such as ethers and esters. Examples of aliphatic solvents include pentanes and hexanes. Examples of aromatic solvents include benzene, xylenes, toluene, and trimethylbenzenes. Examples of ethers include tetrahydrofuran, dioxane, diethyl ether, and polyethers. Examples of esters include ethyl acetate.

In one embodiment, the solvent is toluene (preferably, anhydrous). In another embodiment, the solvent is mesitylene.

If used, the solvent may be added in amounts of 1:1 to 100:1 or 1:1 to 20:1 (v/v), relative to the amount of methanol.

As noted above, to couple methanol with a secondary or tertiary alcohol, the reaction mixture is generally heated to elevated temperatures, for example, from 40 to 160° C. In one embodiment, the reaction is conducted in refluxing benzene, xylene(s), mesitylene, or toluene at atmospheric pressure.

The DHC reaction can take place with catalyst loadings of 225 ppm (0.0025 mol %). For example, the reaction may be carried out with catalyst loadings of 50 to 20,000 ppm (0.005 to 2 mol %), 100 to 15,000 ppm (0.01 to 1.5 mol %), 100 to 10,000 ppm (0.01 to 1 mol %), 100 to 1,000 ppm (0.01 to 0.1 mol %), or 100 to 500 ppm (0.01 to 0.05 mol %).

In accordance with an embodiment of the invention, the catalyst or catalyst precursor(s) is/are combined with methanol and the secondary or tertiary alcohol, and optionally a solvent and/or a hydrogen acceptor, at a catalyst-to-methanol weight ratio of 1:10 to 1:100,000 in a reactor. The mixture is heated with mixing to a temperature of 40 to 160° C. for a period of 1-6 hours during which time hydrogen (H2) may evolve, and may be removed from the reactor. It is possible to carry the reaction to full conversion, but it may be advantageous to limit the conversion due to rates and reaction pressures.

Hydrogen is readily separated from the reaction liquids, which are condensed at this temperature and may be purified and compressed for alternative uses. These operations may be carried out in a batch or continuous mode. A catalyst containing concentrate may be recycled with addition of fresh methanol.

The process according to the invention can produce formate esters with yields of at least 50%, at least 60%, at least 70%, at least 80%, or at least 90%. The reaction times in which these yields may be achieved include 24 hours or less, 12 hours or less, 10 hours or less, 8 hours or less, 6 hours or less, 5 hours or less, 4 hours or less, 3 hours or less, 2 hours or less, or 1 hour or less.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention unless otherwise specifically indicated.

EXAMPLES

General Experimental Information

Unless otherwise noted, all the organometallic compounds were prepared and handled under a nitrogen atmosphere using standard Schlenk and glovebox techniques. Anhydrous methanol (99.7% assay) and toluene were purchased from commercial sources and used without further purification. $^1$H NMR spectra were recorded on Bruker Avance-500 MHz spectrometers. Chemical shift values in $^1$H NMR spectra were referenced internally to the residual solvent resonances. Compounds 1A-C and 3 have been previously reported in the literature and were synthesized according to literature procedures. Ru-MACHO-BH complex (2) and Shvo's catalyst (4) were purchased from Strem Chemicals and used without further purification.

Catalysts

Table 1 shows the catalysts or catalyst precursors used in the following examples.

TABLE 1

| Catalyst Complex | Molecular Structure |
|---|---|
| 1A | [structure of Fe complex with BH$_3$, P($^i$Pr)$_2$, CO, H ligands] |
| 1B | [structure of Fe complex with Br, P($^i$Pr)$_2$, CO, H ligands] |
| 1C | [structure of Fe complex with P($^i$Pr)$_2$, CO, H ligands] |
| 2 | [structure of Ru complex with BH$_3$, PPh$_2$, CO, H ligands] |
| 3 | [structure of pyridine-based Ru complex with Et$_2$N, Cl, P($^t$Bu)$_2$, CO, H ligands] |
| 4 | [structure of Shvo's catalyst - dinuclear Ru complex with Ph groups and CO ligands] |

Selectivity

The selectivity of the product was calculated as the total moles of formate ester produced, as determined by GC-MS (gas chromatography mass spectrometry), divided by the moles of methanol reacted (moles of methanol fed minus moles of methanol left).

Example 1 (Comparative)

A 100-mL stainless steel Parr reactor equipped with a stir bar (400 rpm) was charged with 1A (81 mg, 0.2 mmol, 1 mol %), anhydrous methanol (0.8 mL, 20 mmol), cyclohexanol (CyOH) (8.3 mL, 80 mmol), and 10 mL of anhydrous toluene. The resulting mixture was purged three times with $N_2$ (~150 psig) to remove air and then heated to 100° C. under 250 psig of $N_2$ pressure for 1 hour. After that, the reactor was allowed to cool to room temperature, and $N_2$ gas was slowly vented inside the hood. The sample was analyzed by GC-MS to obtain percent yield and selectivity of cyclohexyl formate (CyOCHO). The results are reported in Table 2.

As seen from Table 2, no desired CyOCHO was produced at 100° C. after one hour. The only product observable by GC-MS was methyl formate.

Example 2 (Comparative)

Example 1 was repeated, except that the reaction time was increased to 16 hours. The results are reported in Table 2.

As seen from Table 2, a longer reaction time did not seem to help the formation of the cyclohexyl formate. Instead of the proposed reaction, β-monomethylation of cyclohexanone (<7%) occurred under these conditions.

Example 3 (Comparative)

Example 1 was repeated, except that the reaction temperature was raised to 140° C. The results are reported in Table 2.

As seen from Table 2, increasing the temperature to 140° C. generated a small amount of cyclohexyl formate (6%) along with the β-monomethylation product (~3%).

Example 4 (Comparative)

Example 1 was repeated, except that the reaction temperature was raised to 160° C. The results are reported in Table 2.

As seen from Table 2, increasing the temperature to 160° C. generated several side products with a slight increase in the percent yield of cyclohexyl formate (8%).

It should be noted that in Examples 1-4, the produced H2 gas could not be flushed out of the reactor due to a limitation with the experimental setup. To circumvent this issue, the following MeOH-CyOH coupling reactions were run in the presence of a sacrificial hydrogen acceptor, methyl methacrylate.

Example 5

Example 3 was repeated, except that methyl methacrylate (8.5 mL, 80 mmol) was also charged to the reactor and the reaction time was increased to 4 hours. The results are reported in Table 2.

As seen from Table 2, surprisingly, when a mixture of MeOH and CyOH (1:4 molar ratio) was heated to 140° C. in toluene in the presence of excess of methyl methacrylate and 1 mol % of 1A, quantitative conversion of methanol was observed in four hours and the desired cyclohexyl formate was produced with 91% yield. Traces of 2-methylcylohexanone and methyl formate were also detected by GC-MS. Noticeably, no external base, which is often used in large excess in other dehydrogenative processes, was required in this reaction.

Example 6

Example 5 was repeated, except that complex 1B was charged to the reactor instead of 1A. The results are reported in Table 2.

Example 7

Example 5 was repeated, except that complex 1C was charged to the reactor instead of 1A. The results are reported in Table 2.

As seen from Table 2, complexes 1B and 1C were less effective and afforded <1% and 69% yield of CyOCHO, respectively. It was not surprising to observe a small amount of product formation with 1B under base-free conditions, because it generally requires one equivalent of base to initiate catalysis.

Example 8

Example 6 was repeated, except that 2 mol % of KOtBu was also charged to the reactor. The results are reported in Table 2.

As seen from Table 2, 89% yield of CyOCHO was produced.

Example 9 (Control)

Example 5 was repeated, except that no catalyst complex was charged to the reactor. The results are reported in Table 2.

As seen from Table 2, no CyOCHO was produced. This control study and the reproducible kinetic behavior without any induction period (R. H. Crabtree et al., Chem. Rev. 2012, 112, 1536) suggest that this system is indeed catalytic in iron and homogeneous in nature.

Example 10

Example 3 was repeated, except that a pressurized autoclave equipped with a back-pressure regulator for the continuous purging of the solution with $N_2$ was used and the reaction time was increased to 24 hours. The results are reported in Table 2.

As seen from Table 2, only trace amounts of CyOCHO was produced.

Example 11

Example 10 was repeated, except that NaOMe (79.10 mmol) was also charged into the reactor. The results are reported in Table 2.

As seen from Table 2, when the MeOH-CyOH coupling reaction was carried out in the presence of an equimolar amount of NaOMe, quantitative conversion of MeOH was observed and P/-methyl cyclohexanol was produced as the sole product.

TABLE 2

Iron-Catalyzed Cross-Coupling of Methanol and Cyclohexanol

| Example | Catalyst | Molar Ratio of MeOH:CyOH:MMA | Time (h) | Temp. (° C.) | CyOCHO Yield (%) | CyOCHO Selectivity (%) |
|---|---|---|---|---|---|---|
| 1 | 1A | 1:4:0 | 1 | 100 | 0 | — |
| 2 | 1A | 1:4:0 | 16 | 100 | 0 | — |
| 3 | 1A | 1:4:0 | 1 | 140 | 6 | — |
| 4 | 1A | 1:4:0 | 1 | 160 | 8 | 61 |
| 5 | 1A | 1:4:4 | 4 | 140 | 91 | 96 |
| 6 | 1B | 1:4:4 | 4 | 140 | <1 | — |
| 7 | 1C | 1:4:4 | 4 | 140 | 69 | 91 |
| 8 | 1B + KO$^t$Bu (2 mol %) | 1:4:4 | 4 | 140 | 89 | 94 |
| 9 | none | 1:4:4 | 4 | 140 | 0 | — |
| 10 | 1A | 1:4 | 24 | 140 | <2 | — |
| 11 | 1A | 1:4 | 24 | 140 | 0 | — |

Example 12

A 100-mL stainless steel Parr reactor equipped with a stir bar (200 rpm) was charged with 1A (81 mg, 0.2 mmol, 1 mol %), anhydrous methanol (0.8 mL, 20 mmol), cyclohexanol (8.3 mL, 80 mmol), methyl methacrylate (8.5 mL, 80 mmol), and 10 mL of anhydrous toluene. The resulting mixture was purged three times with N$_2$ (~150 psig) to remove air and then heated to 140° C. under 250 psig of N$_2$ pressure for 4 hours. After that, the reactor was allowed to cool to room temperature, and N$_2$ gas was slowly vented inside the hood. The sample was analyzed by GC-MS to obtain percent yield and selectivity of cyclohexyl formate (CyOCHO). The results are reported in Table 3.

Example 13

A 100-mL stainless steel Parr reactor equipped with a stir bar (200 rpm) was charged with 1A (81 mg, 0.2 mmol, 1 mol %), anhydrous methanol (0.8 mL, 20 mmol), isopropanol (6.3 mL, 80 mmol), acetone (5.9 mL, 80 mmol), and 10 mL of anhydrous toluene. The resulting mixture was purged three times with N$_2$ (~150 psig) to remove air and then heated to 140° C. under 250 psig of N$_2$ pressure for 4 hours. After that, the reactor was allowed to cool to room temperature and N$_2$ gas was slowly vented inside the hood. The sample was analyzed by GC-MS to obtain percent yield and selectivity of $^i$PrOCHO. The results are reported in Table 3.

Example 14

A 100-mL stainless steel Parr reactor equipped with a stir bar (200 rpm) was charged with 1A (81 mg, 0.2 mmol, 1 mol %), anhydrous methanol (0.8 mL, 20 mmol), propylene glycol propyl ether (10.8 mL, 80 mmol), methyl methacrylate (8.6 mL, 80 mmol), and 10 mL of anhydrous toluene. The resulting mixture was purged three times with N$_2$ (~150 psig) to remove air and then heated to 140° C. under 250 psig of N$_2$ pressure for 4 hours. After that, the reactor was allowed to cool to room temperature and N$_2$ gas was slowly vented inside the hood. The sample was analyzed by GC-MS to obtain percent yield and selectivity of the corresponding formate ester. The results are reported in Table 3.

TABLE 3

Iron-Catalyzed Cross-Coupling of Methanol and Secondary Alcohols

| Example | Secondary Alcohol | Product | Yield (%) | Selectivity (%) |
|---|---|---|---|---|
| 12 | cyclohexanol | cyclohexyl formate | 91 | 96 |
| 13 | isopropanol | isopropyl formate | 83 | >99 |
| 14 | propylene glycol propyl ether (OPr$^n$) | corresponding formate ester (OPr$^n$) | 71 | 90 |

As seen from Table 3, other secondary alcohols including propylene glycol propyl ether (PGPE) and isopropanol ($^i$PrOH) also afforded corresponding formate esters with high yields (Examples 13-14). For the MeOH-$^i$PrOH coupling, the reaction was carried out using acetone as an acceptor instead of methyl methacrylate. Cyclohexanol and PGPE also afforded corresponding formate esters in the presence of acetone, albeit with the coproduction of small amounts of isopropyl formate (generally <10%).

Example 15

A 100-mL stainless steel Parr reactor equipped with a stir bar (200 rpm) was charged with 1A (0.2 mmol, 1 mol %), anhydrous methanol (0.8 mL, 20 mmol), tert-butanol (7.7 mL, 80 mmol), methyl methacrylate (8.6 mL, 80 mmol), and 10 mL of anhydrous toluene. The resulting mixture was purged three times with N$_2$ (~150 psig) to remove air and then heated to 140° C. under 250 psig of N$_2$ pressure for 8 hours. After that, the reactor was allowed to cool to room temperature and N$_2$ gas was slowly vented inside the hood. The sample was analyzed by GC-MS to obtain percent yield and selectivity of $^t$BuOCHO. The results are reported in Table 4.

Example 16

Example 15 was repeated, except that acetone (80 mmol) was used as the hydrogen acceptor instead of methyl methacrylate. The results are reported in Table 4.

Example 17

A 100-mL stainless steel Parr reactor equipped with a stir bar (200 rpm) was charged with 1A (81 mg, 0.2 mmol, 1 mol %), anhydrous methanol (0.8 mL, 20 mmol), 1-methylcyclohexanol (10.3 mL, 80 mmol), methyl methacrylate (8.6 mL, 80 mmol), and 10 mL of anhydrous toluene. The resulting mixture was purged three times with $N_2$ (~150 psig) to remove air and then heated to 140° C. under 250 psig of $N_2$ pressure for 8 hours. After that, the reactor was allowed to cool to room temperature and $N_2$ gas was slowly vented inside the hood. The sample was analyzed by GC to obtain percent yield and selectivity of the corresponding formate ester. The results are reported in Table 4.

TABLE 4

Iron-Catalyzed Cross-Coupling of Methanol and Tertiary Alcohols

| Example | Tertiary Alcohol | Product | Yield (%) | Selectivity (%) |
|---|---|---|---|---|
| 15 | (structure) | (structure) | 72 | >99 |
| 16 | (structure) | (structure) | 63 | 82 |
| 17 | (structure) | (structure) | 44 | 84 |

As seen in Table 4, when a mixture of methanol, ′BuOH, and methyl methacrylate (relative ratio=1:4:4) was heated to 140° C. for 8 h in toluene in the presence of 1 mol % of 1A, ′BuOCHO was produced with a moderately high yield (72%) and a very high selectivity (>99%) (Example 15). No other side product was formed in this coupling reaction. When the same reaction was carried out in the presence of acetone, ~63% ′BuOCHO was produced (Example 16) with concomitant formation of ′PrOCHO as a side product. A reaction between 1-methyl-cyclohexanol and methanol also generated the corresponding formate ester derivative in a moderate yield (Example 17). For this cyclohexyl substrate, β-methylation of the cyclohexyl ring was not observed possibly due to steric reasons.

Example 18 (Comparative)

A 100-mL stainless steel autoclave was charged with Milstein's catalyst 3 (350 mg, 0.7 mmol, 0.009 mol %), KOH (40 mg, 0.7 mmol), methanol (~3.3 mL, 81 mmol), tert-butanol (28.3 mL, 324.2 mmol), and isophorone (42.8 mL, 247.9 mmol). The resulting mixture was purged twice with argon (100 psig) to remove air and finally heated to 133° C. under argon pressure (200 psig) for 6 hours. After that, the reactor was allowed to cool to room temperature and $N_2$ gas was slowly vented inside the hood. The sample was analyzed by GC-MS. The desired ′BuOCHO was not formed.

Milstein's catalyst 3 proved to be unsuccessful in the MeOH-′BuOH coupling reaction in the presence of isophorone as an acceptor.

Reactor Equipment and Setup for Examples 19-20

The reactor was a 100-mL vessel, made of 316 stainless steel, manufactured by Autoclave Engineers. The reactor was equipped with a high-pressure nitrogen source fed through an agitator shaft fitted with a gas dispersion impeller. The reactor included a dip tube for sampling the liquid inside the vessel. The reactor included two independent vent lines from the head space of the vessel that go up to a heat exchanger. The heat exchanger was cooled by a refrigerated glycol bath circulator. After the heat exchanger, there was a micrometer valve for fine nitrogen flow control. This fed a Swagelok back pressure regulator. Gas flow through the system was visibly observed by a rotameter as well as a bubbler. All gases fed through the system exited through a standard Lab Glass dry ice trap to insure no loss of volatile reagents.

Example 19

The 100-mL stainless steel Autoclave Engineers reactor described above fitted with a cold glycerol condenser (24 inches of 0.25 inch OD tubing, −15° C.) was charged with 1A (162 mg, 0.4 mmol), anhydrous methanol (3.2 mL, 80 mmol), cyclohexanol (16.7 mL, 160 mmol), and 20 mL of anhydrous toluene. The resulting mixture was purged three times with $N_2$ (~150 psig) to remove air and then heated to 140° C. under 300 psig of $N_2$ pressure for 6-24 hours. During the reaction, the solution was slowly (0.4-0.5 scfh) purged with nitrogen to remove $H_2$ gas from the system while keeping methanol in the solution phase. After the catalytic reaction was run for approximately 24 hours, the reactor was allowed to cool to room temperature and the $N_2$ gas was slowly vented inside the hood. Trace amounts of cyclohexylformate were detected by GC.

Example 20

Example 19 was repeated, except that NaOMe (4.36 g, 79.10 mmol, 98% purity) was also charged into the reactor. GC-MS analysis was performed on the crude liquid sample. It showed that 2-methylcyclohexanol was formed as the sole product (91.1% yield by GC). This example demonstrates the effect of having too much base present during the reaction.

In the specification, there have been disclosed certain embodiments of the invention and, although specific terms are employed, they are used in a generic and descriptive sense only and not for purposes of limitation, the scope of the invention being set forth in the following claims.

We claim:

1. A process for preparing a formate ester of the formula (X):

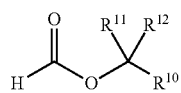

the process comprising contacting anhydrous methanol with an alcohol of the formula (XI):

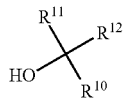

selected from the group consisting of isopropanol, tert-butanol, cyclohexanol, 1-methyl-cyclohexanol, or propylene glycol propyl ether;
in the presence of a catalyst of the formula (I):

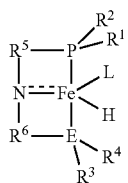

in a reactor at a temperature of 40° C. to 200° C., and a pressure of from atmospheric to 2 MP, and
in the presence of a hydrogen acceptor, selected from the group consisting of acetone, methyl methacrylate, isophorone, or combinations thereof or with the simultaneous removal of hydrogen from the reactor, or both, to form the formate ester of the formula (X),
wherein E is phosphorus or nitrogen;
$R^1$ and $R^2$ are each independently an alkyl, aryl, alkoxy, aryloxy, dialkylamido, diarylamido, or alkylarylamido group having 1 to 12 carbon atoms;
$R^3$ and $R^4$ are each independently an alkyl or aryl group having 1 to 12 carbon atoms, if E is nitrogen;
$R^3$ and $R^4$ are each independently an alkyl, aryl, alkoxy, aryloxy, dialkylamido, diarylamido, or alkylarylamido group having 1 to 12 carbon atoms, if E is phosphorus;
$R^1$, $R^2$, and P may be connected to form a 5 or 6-membered heterocyclic ring;
$R^3$, $R^4$, and E may be connected to form a 5 or 6-membered heterocyclic ring;
$R^5$ and $R^6$ are each independently a $C_1$-$C_6$ alkylene or arylene group;
L is carbon monoxide, a phosphine, an amine, a nitrile, or an N-containing heterocyclic ligand;
$R^{10}$, $R^{11}$, and $R^{12}$ are each independently hydrogen or an alkyl group having 1 to 6 carbon atoms, provided that no more than one of $R^{10}$, $R^{11}$, and $R^{12}$ is hydrogen;
$R^{11}$ and $R^{12}$ may be connected to form a cycloaliphatic group having 4 to 8 carbon atoms; and
$R^{10}$, $R^{11}$, and $R^{12}$ may be connected to form a bicycloaliphatic group having 5 to 14 carbon atoms.

2. The process according to claim 1, wherein one or more of $R^1$, $R^2$, $R^3$, and $R^4$ are substituted with one or more groups selected from ethers, esters, and amides.

3. The process according to claim 1, wherein $R^1$, $R^2$, $R^3$, and $R^4$ are each independently a methyl, ethyl, propyl, isopropyl, butyl, pentyl, isopentyl, cyclopentyl, hexyl, cyclohexyl, or phenyl group.

4. The process according to claim 3, wherein each of $R^1$, $R^2$, $R^3$, and $R^4$ is isopropyl.

5. The process according to claim 3, wherein each of $R^1$, $R^2$, $R^3$, and $R^4$ is phenyl.

6. The process according to claim 1, wherein each of $R^5$ and $R^6$ is —($CH_2CH_2$)—.

7. The process according to claim 1, wherein said temperature is 40 to 160° C.

8. A process for preparing a formate ester of the formula (X):

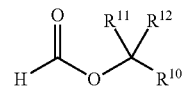

the process comprising contacting anhydrous methanol with an alcohol selected from the group consisting of isopropanol, tert-butanol, cyclohexanol, 1-methyl-cyclohexanol, or propylene glycol propyl ether, in the presence of a catalyst of the formula (I):

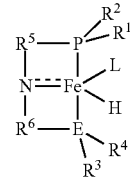

in a reactor at a temperature of 40° C. to 200° C., and a pressure of from atmospheric to 2 MP, to form the formate ester of the formula (X),
in the presence of a hydrogen acceptor, selected from the group consisting of acetone, methyl methacrylate, isophorone, or combinations thereof, or with the simultaneous removal of hydrogen from the reactor, or both, to form the formate ester of the formula (X); and
wherein E is phosphorus or nitrogen;
R1 and R2 are each independently an alkyl, aryl, alkoxy, aryloxy, dialkylamido, diarylamido, or alkylarylamido group having 1 to 12 carbon atoms;
R3 and R4 are each independently an alkyl or aryl group having 1 to 12 carbon atoms, if E is nitrogen;
R3 and R4 are each independently an alkyl, aryl, alkoxy, aryloxy, dialkylamido, diarylamido, or alkylarylamido group having 1 to 12 carbon atoms, if E is phosphorus;
R5 and R6 are each independently a C1-C6 alkylene or arylene group;
L is carbon monoxide, a phosphine compound, an amine compound, an ester compound, a nitrile compound, or an N-containing heterocyclic compound; and
R10, R11, and R12 are each independently hydrogen or an alkyl group having 1 to 6 carbon atoms, provided that no more than one of R10, R11, and R12 is hydrogen.

9. The process of claim 8 wherein said catalyst is:

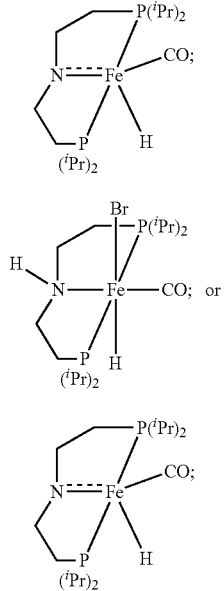

wherein iPr represents an isopropyl group.

10. A process for preparing a formate ester comprising:
contacting anhydrous methanol with an alcohol selected from the group consisting of isopropanol, tert-butanol, cyclohexanol, 1-methyl-cyclohexanol, or propylene glycol propyl ether, in the presence of a catalyst of the formula (IA), (1 B), or (1C):

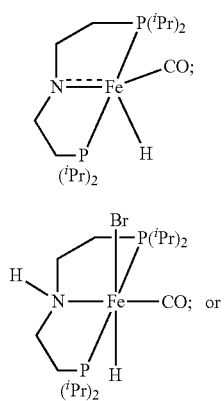

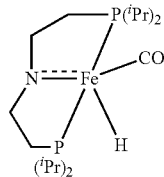

wherein iPr represents an isopropyl group; in a reactor at a temperature of 40° C. to 200° C., and at a pressure of from atmospheric to 2 MP, in the presence of a hydrogen acceptor selected from the group consisting of acetone, methyl methacrylate, isophorone, or combinations thereof, or with the simultaneous removal of hydrogen from the reactor, or both, to form the formate ester of the formula (X):

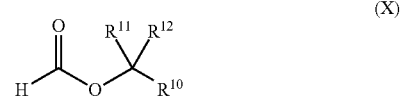

wherein R10, R11, and R12 are each independently hydrogen or an alkyl group having 1 to 6 carbon atoms, provided that no more than one of R10, R11, and R12 is hydrogen.

11. The process of claim 10 further comprising a basic catalyst initiator.

12. The process of claim 11 wherein said catalyst is

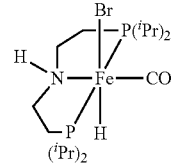

wherein iPr represents an isopropyl group and said catalyst initiator is potassium t-butoxide.

* * * * *